United States Patent [19]

Granger et al.

[11] Patent Number: 5,498,340
[45] Date of Patent: Mar. 12, 1996

[54] PROCESSING OF PROTEIN-CONTAINING BODY FLUIDS

[75] Inventors: Carol A. Granger, Fareham; Gary B. Smith, Portchester; Bruce L. Taylor, Rowlands Castle, all of United Kingdom

[73] Assignee: Pall Corporation, East Hills, N.Y.

[21] Appl. No.: 112,798

[22] Filed: Aug. 27, 1993

[30] Foreign Application Priority Data

Aug. 27, 1992 [GB] United Kingdom ............... 9218239

[51] Int. Cl.$^6$ .......................... B01D 61/00; B01D 61/14
[52] U.S. Cl. .................... 210/645; 210/650; 210/651; 436/177; 436/178; 604/4; 604/5; 604/6
[58] Field of Search ................... 210/641, 645, 210/650, 651, 660, 638, 500.38, 806; 604/4, 5, 6, 28, 29; 436/177, 178

[56] References Cited

U.S. PATENT DOCUMENTS

| | | | |
|---|---|---|---|
| 4,083,786 | 4/1978 | Tsuda et al. | 210/321.6 |
| 4,350,156 | 9/1982 | Malchesky et al. | 210/434 |
| 4,350,594 | 9/1982 | Kawai et al. | 210/641 |
| 4,420,398 | 12/1983 | Castino | 210/641 |
| 4,431,545 | 2/1984 | Pall et al. | 210/641 |
| 4,619,639 | 10/1986 | Nosé et al. | 604/4 |
| 4,663,049 | 5/1987 | Kolff et al. | 210/651 |
| 4,702,840 | 10/1987 | Degen et al. | 210/638 |
| 4,816,162 | 3/1989 | Rosskopf et al. | 210/651 |
| 4,863,603 | 9/1989 | Lehmann et al. | 210/489 |
| 5,015,388 | 5/1991 | Pusineri et al. | 210/641 |

FOREIGN PATENT DOCUMENTS

| | | |
|---|---|---|
| 0479187 | 4/1992 | European Pat. Off. . |
| 3302384 | 7/1984 | Germany . |
| 1374159 | 11/1974 | United Kingdom . |

OTHER PUBLICATIONS

Bruno et al., "Comparison of Spontaneous Ascites Filtration and reinfusion . . . ", British Jrnl. of Medicine, 304, 1655–1658 (1992).

Katoh et al., "Prevention of Febrile Reaction Occurring on Reinfusion . . . ", Japan Jrnl. of Medicine, 30, 311–317 (1991).

Inaba et al., "An Evaluation of Combining Reinfusing Concentrated Ascitic Fluid and . . . ", J. Jpn. Soc. Dial. Ther., 24, 143–149 (1991).

Andoh et al., "Clinical Studies of Reinfusion of Cell–Free & Concentrated Autogenous Ascitic Fluid for Intractable Ascites . . . ", Jpn. J. Haemodial., 20, 931–936 (1987) [English Abstract].

Valbonesi et al., "Reverse Cascade Filtration of Ascitic Fluid–Preliminary Results", Intl. Jrnl. of Artificial Organs, 11, 134–138 (1988).

McMormick et al., "Pathogenesis and Management of Ascites in . . . Liver Disease", Brit. Jrnl. of Hosp. Med., 1992 vol. 47, No. 10, 738–744.

Smart et al., "A randomized prospective trial comparing daily . . . diuretic refractory ascites", Jrnl. of Hepatology, 1990; 10:191–197.

Salem et al., "The Aggregation of Human Platelets by Ascitic . . . ", American Journal of Hematology, 11:153–157 (1981).

*Primary Examiner*—John Kim
*Attorney, Agent, or Firm*—Leydig, Voit & Mayer

[57] ABSTRACT

A protein-containing fluid, for example, ascitic fluid is removed from a patient by paracentesis. The fluid is held in a reservoir and filtered by a plasmapheresis filter and a positively charged nylon membrane before being in a condition for return to the body. This filtration is designed to remove components such as cells, cell fragments, fibrin, endotoxins and other particulate contaminations from the ascitic fluid and thus to reduce the incidence of fever and other unwanted side effects.

13 Claims, 2 Drawing Sheets

PROCESSING OF PROTEIN-CONTAINING BODY FLUIDS

BACKGROUND TO THE INVENTION

1. Field of the Invention

The invention relates to the processing of protein-containing fluids obtained from the body.

In many medical and surgical procedures, protein-containing fluids are drained from the body as a treatment of the body. In general, however, the loss of the protein in the fluid is disadvantageous, because it produces unwanted side-effects. It has been proposed, in some cases, to return the drained fluid to the body, often after filtration and/or other cleansing (e.g. immunoabsorbance), but in general this has not proved entirely satisfactory because of an adverse reaction by the body to the components within the returned fluid.

For example, ascites is the abnormal accumulation of protein-containing fluid in the peritoneal cavity and is frequently encountered in patients with cirrhosis and other forms of severe liver disease. It may also arise in cases of cardiac and renal disease.

2. Brief Review of the Prior Art

Ascites is commonly treated with bed rest, salt restriction and drugs that increase sodium excretion and/or urine output. Drainage of ascitic fluid (paracentesis) may be performed, particularly in cases of advanced cirrhosis when the ascites does not respond to medical intervention.

The ascitic fluid may, in such paracentesis, be drained into the superior vena cava via a surgically implanted peritoneovenous shunt including a one-way valve. Such shunts are, however, associated with a high rate of complications including infection, disseminated intravascular coagulation and thrombosis of the shunt.

In general, therefore, such shunts are avoided and the ascitic fluid is drained out of the patient by paracentesis. Such paracentesis, particularly at large volumes, is associated with hypovolaemia, uraemia and electrolyte disorders since this results in the simultaneous loss of proteins promoting a low protein level. It has been found that these disorders are generally preventable by the simultaneous intravenous infusion of protein in the form of albumen solutions. As indicated in the review by McCormick P. A. and Mcintyre N., [Brit J Hosp Med 47(10): 738–744 (1992)], large volume paracentesis with intravenous colloid infusion is more effective in treating ascites than the standard diuretic therapy with fewer complications and reduced hospital stay.

The use of albumen infusions together with large volume paracentesis has disadvantages. Commercially available albumen is currently largely derived from human plasma with associated high costs, limited availability and the potential untoward effects of infusing blood products. In some countries albumen is poorly available.

A number of studies have described the intravenous infusion of drained ascitic fluid after a variety of processes to remove unwanted substances including excess water.

Bruno et al, [British Medical Journal 304: 1655–1688 (1992)] describe paracentesis by drainage from the peritoneal cavity by gravity into a hemofilter of polyamide fibre (FH88, Gambro, Lund, Sweden) with an effective surface area of 2 $m^2$. The filter filters and concentrates the ascitic fluid separating protein from the water and solutes forming the filtrate. The concentrated ascites is periodically returned to the peritoneal cavity under gravity so that the cavity serves as a mixing chamber for a progressively concentrated ascitic fluid. The concentrate obtained after the last passage is then reinfused through a catheter inserted into an antecubital vein. The filtrate (water and electrolytes) is discarded.

Bruno et al note some cases of fever associated with this procedure and suggest that they are self-limiting. However, Katoh S. et al, [Jpn J Med 30(4) 311–317 (1991)] identify fever as a major problem associated with the intravenous reinfusion of ascites after filtration and concentration and state that the incidence of fever sometimes necessitates the cessation of the reinfusion procedure. Katoh et al suggest that the usefulness of reinfusion of ascites would be increased if this adverse reaction could be overcome.

Katoh et al identify microaggregates, including fibrin, remaining in ascites after filtration and concentration as a cause of such fever. They propose their removal by the use of one of two different types of 40 μm microfilters—either screen filters or depth filters. As a screen filter, Katoh et al use a pleated woven polyester filter having an area of 160 $cm^2$ with a rating of 40 μm and a priming volume of 20 ml. As a depth filter, Katoh et al use a nylon filter with a rating of 0.8 μm and a priming volume of 20 ml.

Katoh et al find little or no reduction of fever by the use of the depth filter but some, although not a total, reduction in fever using a screen filter. Katoh et al thus conclude that some other substance or substances present in the ascites are responsible for the fever. They discuss a number of pyrogenic substances including endotoxins, collagens and cytotoxic polypeptides but fail to locate the substance inducing the febrile reaction.

Fever is also noted as a side effect of intravenous infusion of ascites by Inaba T. et al [J Jpn Soc Dial Ther 24(2): 143–149 (1991)]. This paper refers to the use of screen filters and antipyretics to reduce the incidence of such fever. It also discusses the addition of anti-cancer agents prior to the re-introduction of the filtered ascitic fluid into patients with malignant tumours.

Fibrin is also discussed as a cause of fever and the use of a screen filter to reduce its incidence is mentioned by Andoh T. et al, [Jpn J Haemodial 20(12): 931–936 (1987)].

SUMMARY OF THE INVENTION

According to a first aspect of the invention, there is provided a method for processing protein-containing body fluids comprising passing the fluid to a first filter having a rating for the removal of larger components in the fluid, and then filtering the fluid through a skinless positively charged microporous hydrophilic membrane having a rating less than the rating of the first filter. In a preferred embodiment, the method includes passing the fluid through the first filter, and filtering the fluid through the membrane and removing a pyrogenic substance from the fluid.

According to a second aspect of the invention, there is provided a filtration system for processing protein-containing body fluid comprising a first filter having a rating for the removal of larger components in the fluid and a filtrate outlet in fluid communication with a skinless positively charged microporous hydrophilic membrane having a rating less than the rating of the first filter.

The following is a more detailed description of an embodiment of the invention, by way of example, reference being made to the accompanying drawings, in which:—

DESCRIPTION OF THE PREFERRED EMBODIMENTS

Figure 1:
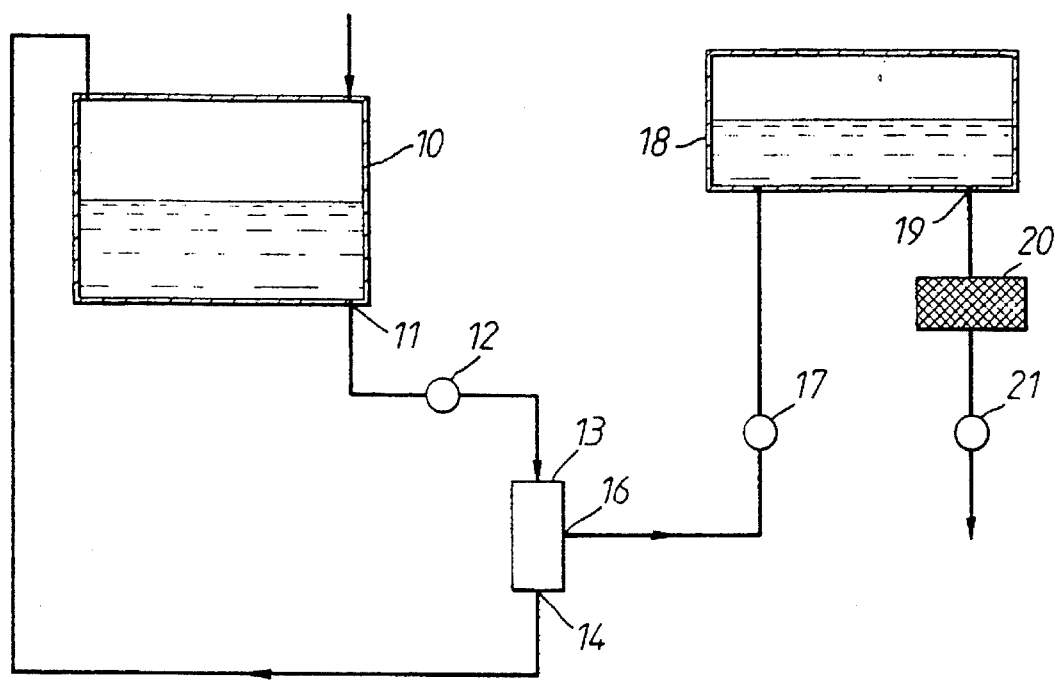
FIG. 1 is a diagram of a first filtration system for processing ascitic fluid.

Referring first to FIG. 1, the filtration system comprises a first reservoir 10 having an outlet 11 connected by a tube to an inlet of a pump, such as a haemofiltration pump 12. A suitable pump includes, but is not limited to, a peristaltic pump. An outlet to the pump is connected to the inlet of a plasmapheresis filter 13. This filter is formed from for example a sheet such as a membrane, or a bundle of hollow fibres and has a 0.3 μm rating. Such a filter is sold by Asahi as the PLASMAFLO OP-05 (Trade Mark). Of course, any other suitable plasmapheresis filter, e.g., a sheet or a bundle of fibers having a suitable pore rating may be used. In general, this rating will be less than 40 μm, preferably less than 20 μm and most preferably less than 5 μm.

The filter 13 has a residue outlet 14 which is connected to the first reservoir 10 to feed residue back to the first reservoir 10. The filter 13 also has a filtrate outlet 16 connected via a second pump 17 to an inlet of a second reservoir 18.

The second reservoir 18 has an outlet 19 which is connected to the inlet of a filter 20 formed by a sheet of skinless positively charged microporous hydrophilic membrane. While a variety of pore ratings may be used, typically, the rating is less than 1 μm, preferably, the membrane has a rating of 0.2 μm. Such a filter is sold by Pall Corporation under the trade mark POSIDYNE CPS-02. Of course other membranes may be used. For example, suitable skinless, positively charged microporous hydrophilic membranes include those disclosed in U.S. Pat. No. 4,702,840.

The outlet 19 to the filter 20 is connected to a third pump 21. Alternatively, the pump 21 could be connected between the outlet 19 to the reservoir 18 and the filter 20.

In use, the system is primed by the use of a suitable priming fluid such as that sold under the trade mark HAEMACCEL. Ascitic fluid from a patient is drained into the first reservoir 10 from which it is passed by the pump 12 to the filter 13. At this filter, plasma proteins, water, and electrolytes are removed from the ascitic fluid. The residue from the filter 13, mainly mammalian cells and concentrated ascitic fluid, is returned to the first reservoir 10. The filtrate, mainly water, plasma protein and electrolytes, is passed by the second pump 17 to the second reservoir 18. Accumulated fluid in the second reservoir 18 is then drawn through the positively charged filter 20 by the third pump 21. Preferably passing the fluid through the positively charged filter includes decreasing the pyrogenic substance content of the filtrate. The resulting filtrate is then ready for intravenous return to the patient.

The filtration system may be topped up with a suitable fluid such as that sold under the trade mark HAEMACCEL during operation.

In one test using the filtration system described above, 4850 ml of ascitic fluid were removed from a patient in 30 hours and 4500 ml (230 g protein) were reinfused during the same period. In that period, 3625 ml of urine was produced.

Examination of the surface of the positively charged membrane of the filter 20 by SEM examination and x-ray emission spectrophometry revealed the presence of organic matter believed to include endotoxins removed as a result of the rating and charge of the filter 20. In addition, the two filters 13,20 together removed cells, bacteria, cell fragments, and fibrin.

It is believed that the removal of these substances including the removal of pyrogenic substances, is likely to reduce or eliminate the incidence of febrile reaction and possibly other side effects in the intravenous reinfusion of ascitic fluids.

In addition, where the fluid includes malignant cells, the rating of the filter 20 is sufficient to remove such cells and so prevent the return to the patient of the malignant cells.

Figure 2:
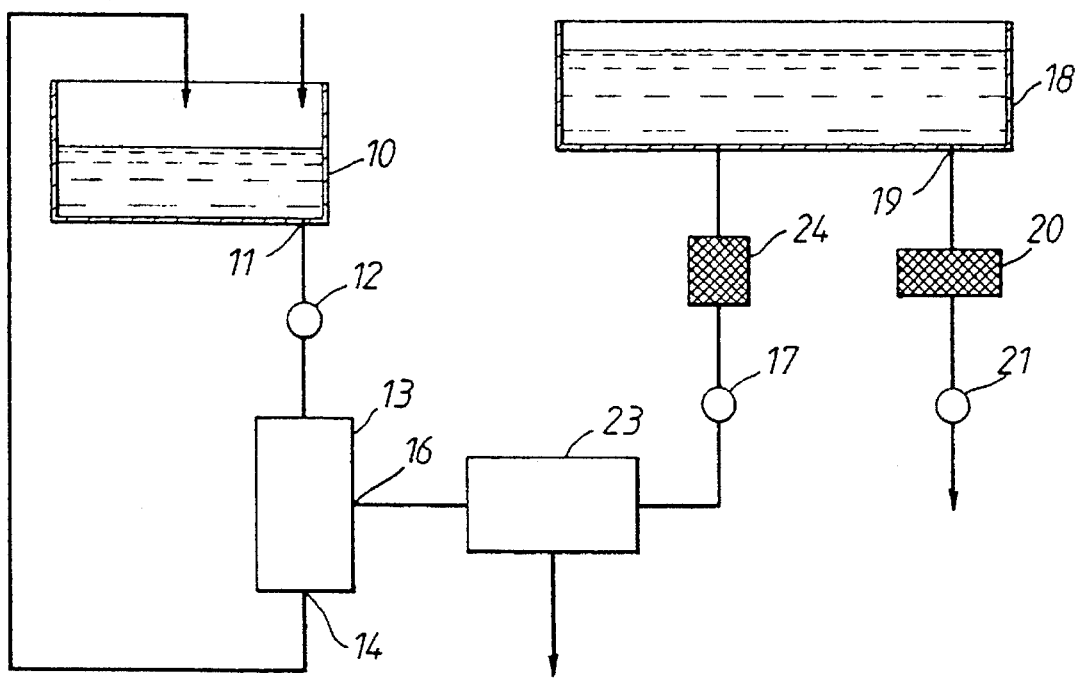
FIG. 2 is a diagram of an alternative form of the system of FIG. 1 including a hemofilter and an affinity column.

It will be appreciated that the system described above with reference to FIG. 1 may be varied in a number of ways. As seen in FIG. 2, where parts common to FIGS. 1 and 2 are given the same reference numerals, a hemofilter 23 and an affinity column 24 may be provided in series between the filter 13 and the second reservoir 18. The hemofilter 23 is of known kind and acts to concentrate the liquid by removing excess water and/or electrolytes, e.g., by ultrafiltration. Suitable hemofilters include, but are not limited to, those sold by Amicon under the trademark Diafilter. The affinity column 24 is of known kind and formed by a matrix on which is immobilised a ligand that is designed to absorb a molecule or group of molecules. For example, where the patient has jaundice, the ligand may absorb the break-down products of haemoglobin. Alternatively, the column may carry antibodies to provide an immunoabsorbtion effect against specified molecules.

Figure 3:
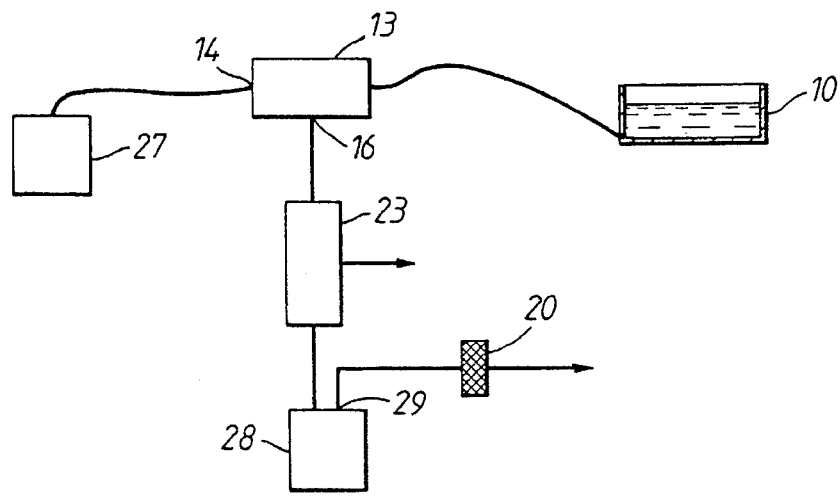
FIG. 3 is a diagram of a second filtration system for processing ascitic fluid and in which the fluid is circulated by gravity.

FIG. 3 shows an alternative embodiment. Parts common to FIG. 3 and to FIGS. 1 and 2 are given the same reference numerals and are not described in detail.

In the embodiment of FIG. 3, the ascitic fluid passes through the system under the force of gravity, so that the pumps 12,17 and/or 21 are omitted. The use of height and/or resistance may be used to affect fluid flow through the system. With respect to height, at least one of the reservoir 10, the patient, and the outlet of filter 20 may be raised or lowered. With respect to resistance, the use of at least one flow control device such as a clamp, may be used to improve the efficiency of fluid flow through the system. For example, at least one roller clamp may be substituted for at least one pump 12, 17 and 21, and the roller clamp may be fully or partially opened and closed to provide the desired flow with respect to 13, 23 and 20. In addition, the second reservoir 18 is omitted. The outlet 14 to the first filter 13 is connected to a bag 27 which collects the residue. The filtrate passes from the outlet 16 to a second bag 28 via a hemofilter 23. An outlet 29 to the second bag 28 is connected to the second filter 20.

Figure 4:
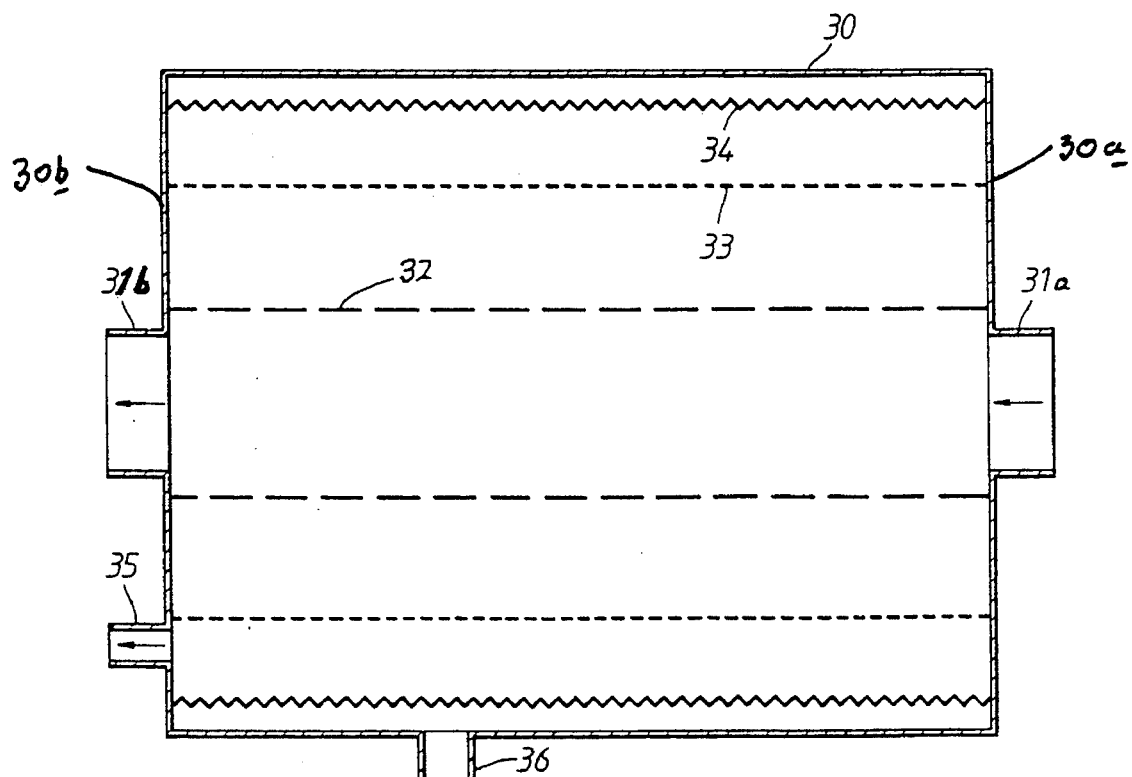
FIG. 4 is a schematic cross-section of a filter unit for use in the systems of any one of FIGS. 1 to 3 and incorporating three filters in series.

The first and second filters 13,20 and, where provided, the hemofilter 23 are connected in series by, for example, tubing. At least one flow control device, such as a clamp, seal, valve, stopcock or the like, may be in or on the tubing. It will be appreciated however, that these filters may be provided in series in a single filter unit. An example of such unit is shown in FIG. 4.

The unit comprises a cylindrical casing 30 having two closed ends 30a and 30b and having a central inlet 31a in one closed end 30a and a central outlet 31b in the other closed end 30b. Within the casing 30 is a radially inner filter 32 which is a sheet of media formed into a tube of circular cross-section and providing a plasmapheresis filter. The media may be the media of the plasmapheresis filter 13, e.g., a sheet such as a membrane as described above with reference to FIG. 1. Radially outwardly of the inner filter 32 is a second filter 33 which is equivalent to the second filter 20 and comprises a sheet of a skinless positively charged microporous hydrophilic membrane formed into a tube of circular cross-section. The membrane may be the membrane of the filter 20 as described above with reference to FIG. 1 with a rating of 0.2 μm. The space between the filters 32,33 forms a reservoir which holds filtered fluid from the plasmapheresis filter 32 before its passage through the second filter 33. The inner and second filters 32,33 are co-axial with each other and with the axis of the casing 30.

Radially outwardly of the second filter 33 is a third filter 34 formed as a sheet of filter membrane formed into a tube of circular cross-section and providing the hemofilter 23 described above with reference to FIG. 1. The material of this membrane may be cellulose acetate, cellulose nitrate, polysulphone or polyacrylonitrite or any other suitable material known for this purpose. The rating of the membrane may be 0.3 μm.

A second outlet 35 is provided in one closed end 30b of the casing 30 leading from the cylindrical reservoir space between the second and third filters 33 and 34. A third outlet 36 is provided in the casing 30 leading from the cylindrical reservoir space between the third filter 34 and the casing 30.

In use, ascitic fluid from, for example, the patient, enters the inlet 31a and the fluid is filtered through the plasmapherisis filter of the first filter 32 and the positively charged microporous hydrophilic membrane of the second filter 33. The filtered ascitic fluid, with cells, cell fragments, fibres and endotoxins removed, then enters the space between the second and third filters 33,34. The hemofilter of the third filter 34 then removes excessive water and electrolytes which leave via the third outlet 36. The concentrated fluid then leaves leaving the second outlet 35 after which it can be returned to a patient, as described above. The residue passing through the outlet 31b and/or the fluid passing through the outlet 36 may, if desired, be retained, e.g., returned to the reservoir for recirculation.

As described with respect to FIG. 3, the unit may be used with gravity flow, i.e., by varying height and/or resistance. The filter unit may be used with at least one pump. Preferably, the unit is used with at least one flow control device, operatively associated with at least one of inlet 31a, outlet 31b, outlet 35 and outlet 36. In a preferred embodiment, a flow control device is located between outlet 35 and the patient. In a more preferred embodiment, flow control devices are downstream of outlets 31b and 36. The flow control devices may be fully or partially opened or closed to provide the desired flow with respect to 32, 33 and 34.

The systems described above with reference to the drawings are for the processing of ascitic fluid removed by abdominal paracentesis. Any one of them could, however, also be used to process ascitic fluid removed from the abdomen by surgery.

In addition, the systems could be used for processing other protein-containing body fluids before intravenous re-infusion and some examples are given below:—

1. The recovery of protein-containing fluids from the pleural cavity.

2. The recovery of protein-containing fluid from that drained in patients with chylothorax.

3. The recovery of protein-containing fluid from peritoneal dialysis fluid or peritoneal lavage fluid.

4. The recovery of protein-containing fluid from blood losses lost from the urinary tract after urological surgery such as transurethral resection of the prostate.

5. The recovery of plasma-containing fluid from the red cell washing fluids used in certain autotransfusion techniques.

6. The recovery of plasma-containing fluid from blood removed from patients at exchange transfusions.

7. The recovery of plasma-containing fluid from blood lost from operative sites where red cell salvage is impractical or undesirable such as in drainage from retroperitoneal haemotoma or large haemothorax.

8. The recovery of plasma-containing fluid from fluid lost from extensive tissue injury as in the early phase of severe burns.

9. The recovery of plasma-containing fluid from cerebrospinal fluid drained from the subarachnoid space.

In all these cases, it is not possible to return the drained fluid to the body because it contains substances that are likely to produce an adverse reaction. Such substances include, but are not limited to, cells, cell debris, fibrin, endotoxins, collagens, bacteria and cytotoxic polypeptides. Preferably, the substances include pyrogenic substances. The use of the system described above with reference to the drawing removes those substances and allows the protein-containing portion of the fluid to be returned to the body without adverse reaction.

Filter ratings are as quoted by their manufacturers. The afore-mentioned POSIDYNE filter is validated by liquid bacterial challenge using the industry-standard organism, *Pseudomonas diminutia*. The test procedure involves:

(i) growing a culture of the organism in water to a known concentration, (ii) flowing the culture through the test filter and collecting the effluent on an analysis disc downstream of the test filter, (iii) plating out the analysis disc on a solid agar growth medium, (iv) incubating the growth medium at 32° C. for three days, and then (v) counting the number of growth colonies on the growth medium.

The removal efficiency of the filter is given by the expression,

Efficiency, $\% = 100(1 - 1/T_R)$, where $T_R$ is titre reduction defined as the ratio of *Pseudomonas diminutia* content in the influent to the number of growth colonies in the effluent.

We claim:

1. A method for processing protein-containing ascites fluid from a body comprising:

passing the protein-containing ascites fluid to a first filter having a pore rating for the removal of cells in the fluid, and then filtering the protein-containing cell-depleted fluid through a skinless positively charged microporous hydrophilic membrane having a pore rating less than the rating of the first filter to produce a protein-containing fluid for infusion into the body.

2. A method as claimed in claim 1 comprising passing the protein-containing cell-depleted fluid from the first filter to a reservoir, and then passing the fluid from the reservoir to the skinless positively charged microporous hydrophilic membrane.

3. A method as claimed in claim 1, comprising holding the protein-containing ascites fluid in a reservoir, passing the fluid from said reservoir to the first filter and passing cell containing fluid from the first filter back to said reservoir.

4. A method as claimed in claim 1 comprising passing the cell containing fluid from the first filter to storage means.

5. A method as claimed in claim 1 comprising passing the protein-containing cell-depleted fluid through a water removing filter between the first filter and the skinless positively charged microporous hydrophilic membrane.

6. A method as claimed in claim 1 comprising passing the protein-containing cell-depleted fluid through an affinity column between the first filter and the skinless positively charged microporous hydrophilic membrane.

7. A method as claimed in claim 1 comprising passing the protein-containing ascites fluid through the first filter and the protein-containing cell-depleted fluid through the skinless positively charged microporous hydrophilic membrane arranged in succession in a fluid flow path through a single filter unit.

8. A method as claimed in claim 7 comprising passing the protein-containing fluid through a water removing filter arranged in the unit in the fluid flow path and downstream of the skinless positively charged microporous hydrophilic membrane.

9. A method as claimed in claim 1 wherein the pore rating of the skinless positively charged microporous hydrophilic membrane is 0.2 μm.

10. The method of claim 1 further comprising returning the protein containing fluid to a patient.

11. A method for processing ascites fluid containing plasma proteins and cells comprising:

filtering the ascites fluid to separate plasma protein-containing fluid from cell-containing fluid;

removing a pyrogenic substance from the separated plasma protein-containing fluid by passing the fluid through a skinless positively charged microporous hydrophilic membrane.

12. The method of claim 11 further comprising recovering the cell-containing fluid.

13. The method of claim 11 further comprising removing ascites fluid containing plasma proteins and cells from a body, and returning the pyrogen-depleted plasma protein-containing fluid to the body.

* * * * *